United States Patent
Lin et al.

(10) Patent No.: US 9,895,110 B2
(45) Date of Patent: *Feb. 20, 2018

(54) EXERCISE PHYSIOLOGICAL SENSING SYSTEM, MOTION ARTIFACT SUPPRESSION PROCESSING METHOD AND DEVICE

(71) Applicant: Industrial Technology Research Institute, Hsinchu (TW)

(72) Inventors: Hsing-Chen Lin, Taichung (TW); Shuenn-Yuh Lee, Tainan (TW); Tzung-Min Tsai, Changhua County (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/519,147

(22) Filed: Oct. 21, 2014

(65) Prior Publication Data

US 2016/0073963 A1  Mar. 17, 2016

(30) Foreign Application Priority Data

Sep. 11, 2014  (TW) .............................. 103131327 A (51) Int. Cl.
*A61B 5/00* (2006.01)
*A61B 7/04* (2006.01)
(Continued)

(52) U.S. Cl.
CPC ........ *A61B 5/7207* (2013.01); *A61B 5/02438* (2013.01); *A61B 5/02444* (2013.01);
(Continued)

(58) Field of Classification Search
CPC .................................................. A61B 5/6816
See application file for complete search history.

(56) References Cited

U.S. PATENT DOCUMENTS 6,783,501 B2  8/2004  Takahashi et al.
7,769,435 B2  8/2010  Kuo et al.
(Continued)

FOREIGN PATENT DOCUMENTS

TW  M245952  10/2004
TW  I222861  11/2004
(Continued)

OTHER PUBLICATIONS

"Notice of Allowance of Taiwan Counterpart Application", dated Jun. 20, 2016, p. 1-p. 3, in which the listed references were cited.
(Continued)

*Primary Examiner* — Carl H Layno
*Assistant Examiner* — Jennifer Ghand
(74) *Attorney, Agent, or Firm* — JCIPRNET (57) ABSTRACT

An exercise physiological sensing system, a motion artifact suppression processing method and a motion artifact suppression processing device for obtaining a stable exercise heart rate signal of a user during exercise are provided. The exercise physiological sensing system includes a bone conduction object, a signal-to-noise ratio analysis module, and a computation module. The bone conduction object has a physiological sensor. The physiological sensor detects a physiological signal of otic bones of the user. The signal-to-noise ratio analysis module is coupled to the physiological sensor and detects a stability of the physiological signal of the otic bones. The computation module is coupled to the signal-to-noise ratio analysis module and generates the stable exercise heart rate signal according to the physiological signal of the otic bones. Accordingly, the exercise physiological sensing system can effectively improve the detected stability of an exercise physiological signal.

6 Claims, 7 Drawing Sheets

(51) Int. Cl.
*A61B 5/024* (2006.01)
*H04R 1/46* (2006.01)

(52) U.S. Cl.
CPC .......... *A61B 5/6803* (2013.01); *A61B 5/6816* (2013.01); *A61B 7/04* (2013.01); *H04R 1/46* (2013.01); *A61B 5/725* (2013.01); *A61B 2562/0204* (2013.01); *A61B 2562/028* (2013.01); *H04R 2201/003* (2013.01)

(56) References Cited

U.S. PATENT DOCUMENTS

| | | |
|---|---|---|
| 2003/0018274 A1 | 1/2003 | Takahashi et al. |
| 2003/0220584 A1* | 11/2003 | Honeyager ........ A61B 5/02125 600/559 |
| 2003/0233051 A1* | 12/2003 | Verjus ................ A61B 5/02438 600/528 |
| 2007/0014423 A1* | 1/2007 | Darbut .................. H04R 25/65 381/330 |
| 2007/0219059 A1 | 9/2007 | Schwartz et al. |
| 2007/0219457 A1* | 9/2007 | Lo ........................ A61B 5/0002 600/519 |
| 2009/0060231 A1 | 3/2009 | Buroojy |
| 2010/0016741 A1 | 1/2010 | Mix et al. |
| 2010/0210420 A1 | 8/2010 | Chang et al. |
| 2012/0232418 A1* | 9/2012 | Kimura .............. A61B 5/02411 600/528 |
| 2013/0022220 A1 | 1/2013 | Dong et al. |
| 2016/0051150 A1* | 2/2016 | Aarts ..................... A61B 5/021 600/485 |

FOREIGN PATENT DOCUMENTS

| | | |
|---|---|---|
| TW | 200719867 | 6/2007 |
| TW | I316401 | 11/2009 |
| TW | 201036591 | 10/2010 |
| TW | I374726 | 10/2012 |

OTHER PUBLICATIONS

Jun Tokuda, et al., "Development of an earphone-like pulsimeter and walking application," SICE Annual Conference 2008, Aug. 20-22, 2008, pp. 2304-2307.

Masaki Shuzo, et al., "Discrimination of Eating Habits with a Wearable Bone Conduction Sound Recorder System," Sensors, 2009 IEEE, Oct. 25-28, 2009, pp. 1666-1669.

Keya Pandia, et al., "Motion Artifact Cancellation to Obtain Heart Sounds From a Single Chest-Worn Accelerometer," Acoustics Speech and Signal Processing (ICASSP), 2010 IEEE International Conference on, Mar. 14-19, 2010, pp. 590-593.

Ming-Zher Poh, et al., "Cardiovascular Monitoring Using Earphones and a Mobile Device," Pervasive Computing, IEEE, vol. 11, Issue 4, Dec. 3, 2010, pp. 18-26.

Ji Yun Shin, et al., "Development of Smartphone-based Stethoscope System," Control, Automation and Systems (ICCAS), 2013 13th International Conference on, Oct. 20-23, 2013, pp. 1288-1291.

* cited by examiner

EXERCISE PHYSIOLOGICAL SENSING SYSTEM, MOTION ARTIFACT SUPPRESSION PROCESSING METHOD AND DEVICE

CROSS-REFERENCE TO RELATED APPLICATION

This application claims the priority benefit of Taiwan application serial no. 103131327, filed on Sep. 11, 2014. The entirety of the above-mentioned patent application is hereby incorporated by reference herein and made a part of this specification.

TECHNICAL FIELD

The present disclosure relates to an exercise physiological sensing system, a motion artifact suppression processing method and a motion artifact suppression processing device for obtaining a stable exercise heart rate signal of a user during exercise.

BACKGROUND

In recent years, people have become more conscious concerning the issues of health, and thus population for engaging exercises (such as hiking, jogging, walking and biking) is also gradually increased each year. For instance, when a high-intensity self-training is to be conducted, a jogger may want to know about changes in physiological status and whether exercise intensity can achieve a personal fitness goal. As such, the jogger may wear various physiological recorders (e.g., a health watch, a pace recorder and a heart rate belt, etc.) in order to constantly monitor the physiological status. To prevent errors from occurring on exercise physiological data measured in a high-intensity exercise-training, the auxiliary devices worn by the jogger must be in close contact with the skin of the jogger. However, this results in discomfort for the user during exercise and thereby reduces willingness in equipping or wearing said devices.

Accordingly, it is one of the major subjects in the industry as how solve the discomfort for the user during exercise while improving a stability of the exercise physiological data measured in the high-intensity self-training.

SUMMARY

The present disclosure is directed to an exercise physiological sensing system, a motion artifact suppression processing method and a motion artifact suppression processing device, which are capable of monitoring a stable exercise heart rate signal of a user during exercise.

An exercise physiological sensing system for obtaining a stable exercise heart rate signal of a user during exercise is provided according to an exemplary embodiment of the present disclosure. The exercise physiological sensing system includes a bone conduction object, a signal-to-noise ratio analysis module, and a computation module. The bone conduction object has a physiological sensor. The physiological sensor detects a physiological signal of otic bones of the user. The signal-to-noise ratio analysis module is coupled to the physiological sensor and detects a stability of the physiological signal of the otic bones. The computation module is coupled to the signal-to-noise ratio analysis module and generates the stable exercise heart rate signal according to the physiological signal of the otic bones.

A motion artifact suppression processing method for processing a physiological signal of otic bones of a user detected during exercise is provided according to an exemplary embodiment of the present disclosure. The motion artifact suppression processing method includes: placing an otic bones exercise digital signal into a sample matrix, and initializing a basis matrix and a coefficient matrix and normalizing the basis matrix. The motion artifact suppression processing method further includes: updating values of a plurality of elements of the basis matrix according to original values of the elements of the basis matrix and updating values of a plurality of elements of the coefficient matrix according to original values of the elements of the coefficient matrix. The motion artifact suppression processing method further includes: when the values of the elements in both the basis matrix and the coefficient matrix are fully updated, calculating a mean square error (MSE) according to the basis matrix, the coefficient matrix and the sample matrix, and obtaining a motion artifact and an exercise heart rate signal according to the mean square error. If the values of the elements in both the basis matrix and the coefficient matrix are not yet fully updated, the operation of updating the values of the elements of the basis matrix according to the original values of the elements of the basis matrix and updating the values of the elements of the coefficient matrix according to the original values of the elements of the coefficient matrix is re-executed.

A motion artifact suppression processing device for processing a physiological signal of otic bones of a user detected during exercise is provided according to an exemplary embodiment of the present disclosure. The motion artifact suppression processing device includes a signal input module, a processing and computation module, and a signal output module. The signal input module receives an otic bones exercise digital signal. The processing and computation module is coupled to the signal input module and places an otic bones exercise digital signal into a sample matrix. In addition, the processing and computation module further initializes a basis matrix and a coefficient matrix and normalizes the basis matrix. Furthermore, the processing and computation module further updates values of a plurality of elements of the basis matrix according to original values of the elements of the basis matrix and updates values of a plurality of elements of the coefficient matrix according to original values of the elements of the coefficient matrix. When the values of the elements in both the basis matrix and the coefficient matrix are fully updated, the processing and computation module further calculates a mean square error according to the basis matrix, the coefficient matrix and the sample matrix, and obtains a motion artifact and an exercise heart rate signal according to the mean square error. The signal output module is coupled to the processing and computation module and output the motion artifact and the exercise heart rate signal. If the values of the elements in both the basis matrix and the coefficient matrix are not yet fully updated, the operation of updating the values of the elements of the basis matrix according to the original values of the elements of the basis matrix and updating the values of the elements of the coefficient matrix according to the original values of the elements of the coefficient matrix is re-executed by the processing and computation module.

Based on the above, the exercise physiological sensing system, the motion artifact suppression processing method and the motion artifact suppression processing device proposed according to the exemplary embodiments of the present disclosure are capable of improving the stability of the exercise physiological data detected in the high-intensity exercise training by detecting the physiological signal of the otic bones of the user.

To make the above features and advantages of the present disclosure more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

[First Exemplary Embodiment]

Figure 1:
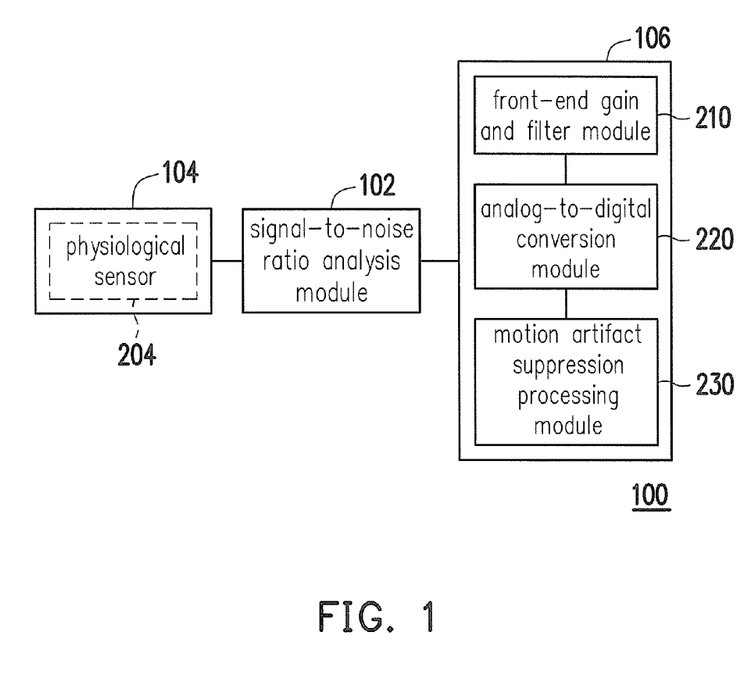
FIG. 1 is a schematic diagram illustrating an exercise physiological sensing system according to a first exemplary embodiment of the present disclosure.

FIG. 1 is a schematic diagram illustrating an exercise physiological sensing system according to a first exemplary embodiment of the present disclosure.

Referring to FIG. 1, an exercise physiological sensing system 100 is configured to assist in detecting and processing a physiological signal of the user during exercise, especially obtaining a stable exercise heart rate signal of a user during exercise. For example, the exercise physiological sensing system 100 may be implemented in an exercise physiological sensing device used in various exercises such as a stepping exercise, a running exercise, a jogging exercise or a biking exercise, but the present disclosure is not limited to thereto.

It should be noted that, for clear description, in the present exemplary embodiment, an exercise physiological sensing device implemented for running exercise is provided below as an example for description in detail.

Figure 2A:
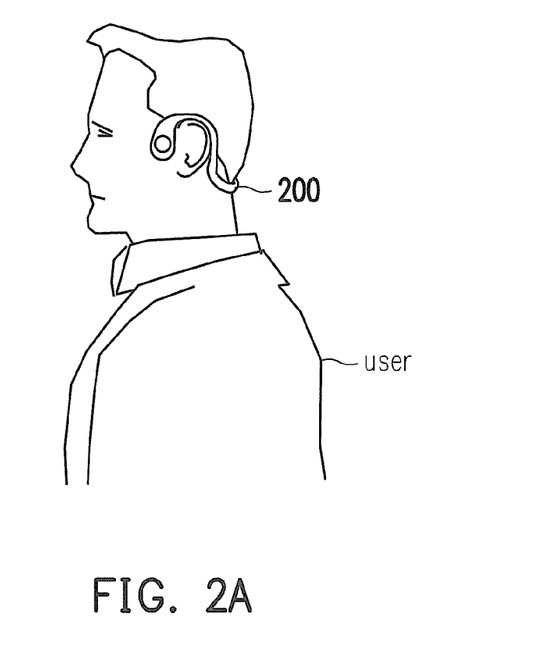
FIG. 2A and FIG. 2B are schematic diagrams illustrating the exercise physiological sensing system implemented in an exercise physiological sensing device according to the first exemplary embodiment of the present disclosure.
Figure 2B:
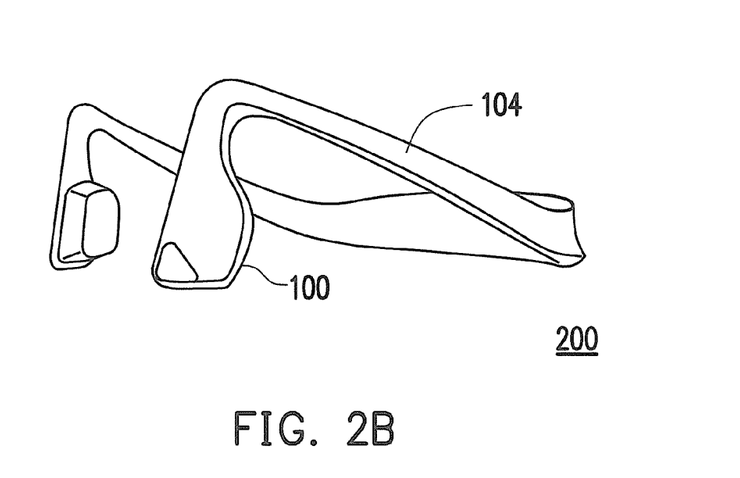

FIG. 2A and FIG. 2B are schematic diagrams illustrating the exercise physiological sensing system implemented in an exercise physiological sensing device according to the first exemplary embodiment of the present disclosure.

Referring to FIG. 2A and FIG. 2B, an exercise physiological sensing device 200 is disposed at otic bones of the user during exercise, and the exercise physiological sensing system 100 implemented in the exercise physiological sensing device 200 has a bone conduction object 104. For example, in the present exemplary embodiment, the bone conduction object 104 is a mobile device.

The exercise physiological sensing system 100 is configured to detect a physiological signal of the otic bones of the user. Further, the mobile device provides functions to play music or radio programs. For example, after the exercise physiological sensing device 200 is disposed at the otic bones so that the exercise physiological sensing system 100 is attached closely to the otic bones of the user. The exercise physiological sensing system 100 can not only constantly monitor physiological status of the user during exercise, but also the user may use the functions to play music or radio programs which are provided by the device.

The mobile device can be connected to an electronic device (e.g., a personal digital assistant (PDA), a notebook computer, a tablet computer or a desktop computer, etc.) by a wired or wireless manners. Accordingly, the user is able to instantly obtain and store the stable exercise heart rate signal during exercise. Particularly, with this disposition of the mobile device, the user is able to be aware of surrounding sounds, so that the safety during exercise can be improved.

Referring back to FIG. 1, the exercise physiological sensing system 100 includes the bone conduction object 104, a signal-to-noise ratio analysis module 102, and a computation module 106.

The bone conduction object 104 has a physiological sensor 204. For example, in the present exemplary embodiment, the physiological sensor 204 is a bone conduction microphone, and the physiological sensor 204 is capable of detecting the physiological signal of the otic bones of the user. It is worth mentioning that, the bone conduction microphone receives a sound signal of bone vibration through the bone-skin conduction with the user (i.e., the otic bones of the user). Therefore, interferences of sounds from both the human body and the surroundings can be effectively reduced. In other words, by utilizing a characteristic of excellent anti-noise and anti-interference provided by the bone conduction microphone, a process of noise and interference elimination can be performed on the received physiological signal of the otic bones in advance.

The signal-to-noise ratio analysis module 102 is coupled to the physiological sensor 204 and configured to detect a stability of the physiological signal of the otic bones received by the physiological sensor 204. For example, in the present exemplary embodiment, the physiological signal of the otic bones is detected by the bone conduction microphone. Therefore, the signal-to-noise ratio analysis module 102 can determine that the quality of the physiological signal of the otic bones is excellent.

The computation module 106 is coupled to the signal-to-noise ratio analysis module 102 and configured to generate the stable exercise heart rate signal according to the physiological signal of the otic bones received by the signal-to-noise ratio analysis module 102.

For example, in the present exemplary embodiment, the computation module 106 includes a front-end gain and filter module 210, an analog-to-digital conversion module 220 and a motion artifact suppression processing module 230.

The front-end gain and filter module 210 filters and amplifies the physiological signal of the otic bones received by the signal-to-noise ratio analysis module 102 in order to generate the otic bones exercise analog signal, and transmits this otic bones exercise analog signal to the analog-to-digital conversion module 220. Subsequently, the analog-to-digital conversion module 220 converts the otic bones exercise analog signal into an otic bones exercise digital signal, and transmits this otic bones exercise digital signal to the motion artifact suppression processing module 230. Thereafter, the motion artifact suppression processing module 230 further decomposes the otic bones exercise digital signal at least into a motion artifact and an exercise heart rate signal, and eliminates the decomposed motion artifact from the otic bones exercise digital signal in order to obtain the stable exercise heart rate signal.

It should be noted that, the motion artifact suppression processing module 230 in the computation module 106 of the present disclosure is implemented by software modules or program codes. For example, the exercise physiological sensing system 100 may include a processor circuit (not illustrated) and a storage circuit (not illustrated) that is configured to store the program codes for executing functions of the motion artifact suppression processing module 230 in the computation module 106. Later, when the exercise physiological sensing system 100 is enabled, the software program codes are loaded from the storage circuit and executed by the processor circuit in order to perform the functions of the motion artifact suppression processing module 230 in the computation module 106. However, the present disclosure is not limited thereto. For example, in another exemplary embodiment of the present disclosure, the signal-to-noise ratio analysis module 102, the computation module 106 as well as the front-end gain and filter module 210, the analog-to-digital conversion module 220 and the motion artifact suppression processing module 230 thereof may be implemented by hardware circuits. For example, functions of the signal-to-noise ratio analysis module 102, the computation module 106, the front-end gain and filter module 210, the analog-to-digital conversion module 220 and the motion artifact suppression processing module 230 may be implemented by the hardware circuits to become a signal-to-noise ratio analysis circuit, a computation circuit, a front-end gain and filter circuit, an analog-to-digital conversion circuit and a motion artifact suppression processing circuit.

Figure 3:
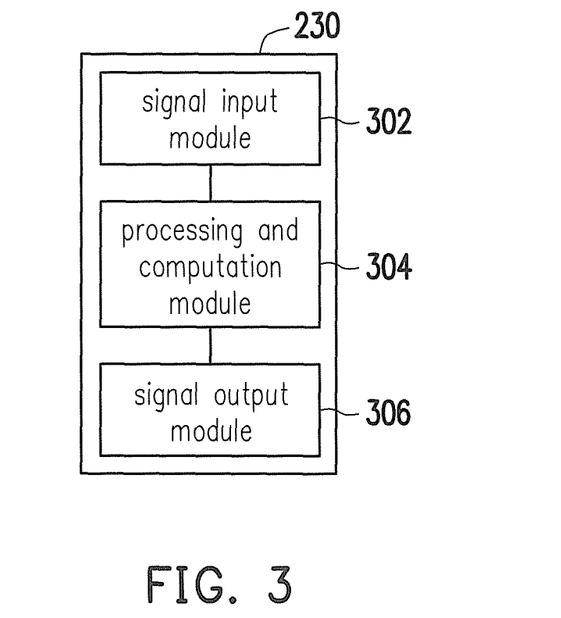
FIG. 3 is a block diagram illustrating the motion artifact suppression processing module according to the first exemplary embodiment of the present disclosure.

FIG. 3 is a block diagram illustrating the motion artifact suppression processing module according to the first exemplary embodiment of the present disclosure.

Referring to FIG. 3, the motion artifact suppression processing module 230 includes a signal input module 302, a processing and computation module 304, and a signal output module 306. The signal input module 302 receives the otic bones exercise digital signal from the analog-to-digital conversion module 220, and transmits the otic bones exercise digital signal to the processing and computation module 304. The processing and computation module 304 is coupled to the signal input module 302, and the signal output module 306 is coupled to the processing and computation module 304.

In the exemplary embodiments of the present disclosure, the operation of the motion artifact suppression processing module 230 for decomposing the otic bones exercise digital signal at least into the motion artifact and the exercise heart rate signal includes the following. First of all, the processing and computation module 304 places the otic bones exercise digital signal into a sample matrix. Subsequently, the processing and computation module 304 initializes a basis matrix and a coefficient matrix and normalizes the basis matrix. Thereafter, the processing and computation module 304 updates values of a plurality of elements of the basis matrix according to original values of the elements of the basis matrix and updates values of a plurality of elements of the coefficient matrix according to original values of the elements of the coefficient matrix. When the values of the elements in both the basis matrix and the coefficient matrix are fully updated, the processing and computation module 304 further calculates a mean square error according to the basis matrix, the coefficient matrix and the sample matrix. Then, the processing and computation module 304 obtains the motion artifact and the exercise heart rate signal according to the mean square error, and the motion artifact and the exercise heart rate signal are outputted by the signal output module 306.

More specifically, in the operation of the processing and computation module 304 for initializing the basis matrix and the coefficient matrix, the processing and computation module 304 ensures that values of a plurality of elements in both the basis matrix and the coefficient matrix are not negative values. Moreover, in the operation of the processing and computation module 304 for normalizing the basis matrix, the processing and computation module 304 normalizes a column vector of the basis matrix until a sum of a plurality of elements corresponding to the column vector is 1.

When the values of the elements in both the basis matrix and the coefficient matrix are fully updated, the processing and computation module 304 replaces the original values of the elements in both the basis matrix and the coefficient matrix respectively by the updated values of the elements. Thereafter, the processing and computation module 304 also executes the operation of normalizing the basis matrix in order to normalize the column vector of the basis matrix until the sum of the elements corresponding to the column vector is 1. Further, the processing and computation module 304 calculates the mean square error according to a product of the basis matrix and the coefficient matrix and the sample matrix. It should be noted that, if the values of the elements in both the basis matrix and the coefficient matrix are not yet fully updated, the processing and computation module 304 continues to execute the operation of updating the values of the elements of the basis matrix according to the original values of the elements of the basis matrix and updating the values of the elements of the coefficient matrix according to the original values of the elements of the coefficient matrix until the values of all the elements in the basis matrix and the coefficient matrix are fully updated.

Particularly, in the operation of obtaining the motion artifact and the exercise heart rate signal according to the mean square error, if the mean square error is 0 or a value of the mean square error is no longer changing, the processing and computation module 304 obtains the motion artifact and the exercise heart rate signal according to the current basis matrix, the current coefficient matrix and the current sample matrix. Otherwise, if the mean square error is not 0 or the value of the mean square error is constantly changing, the processing and computation module 304 re-executes the operation of updating the values of the elements of the basis matrix according to the original values of the elements of the basis matrix and updating the values of the elements of the coefficient matrix according to the original values of the elements of the coefficient matrix.

Figure 4:
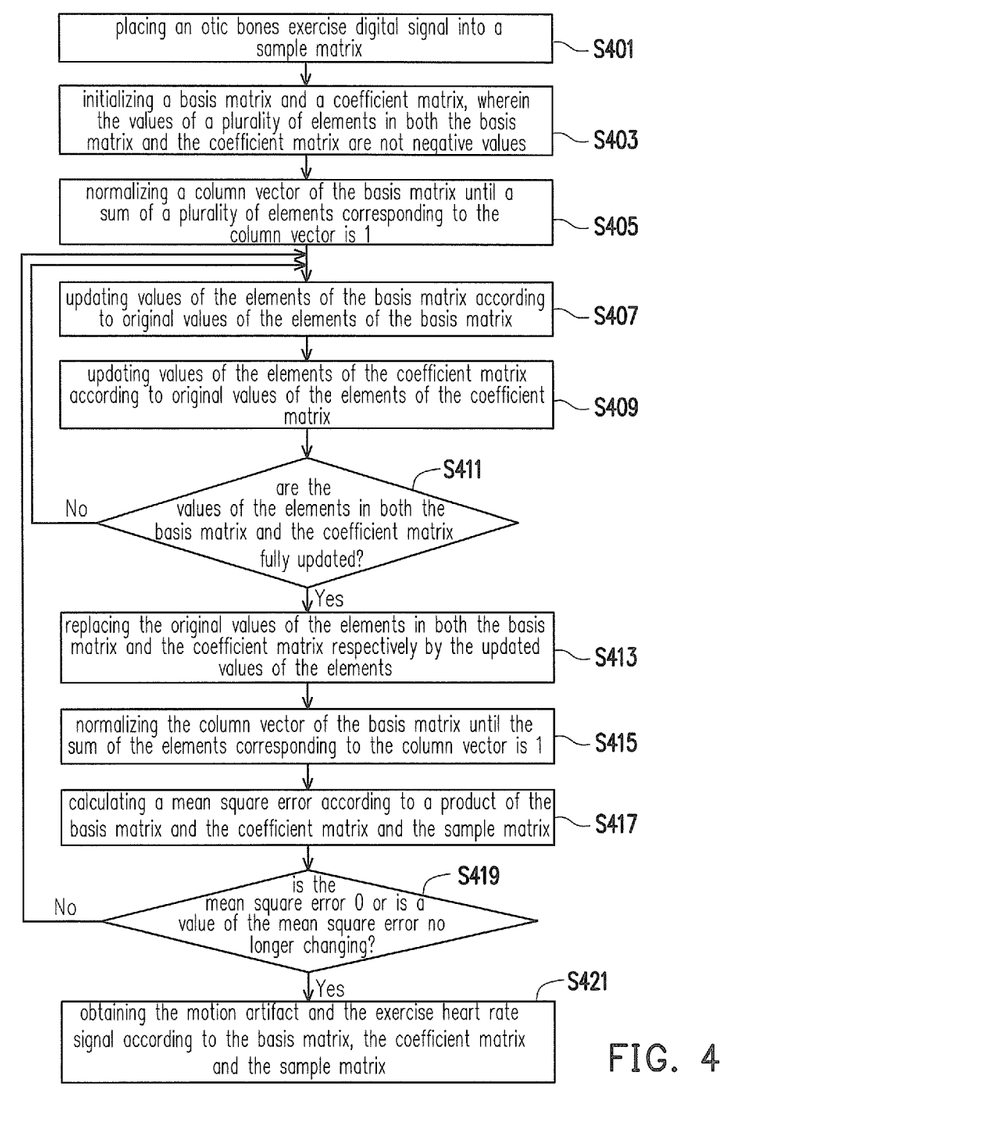
FIG. 4 is a flowchart illustrating a motion artifact suppression processing method according to the first exemplary embodiment of the present disclosure.

FIG. 4 is a flowchart illustrating a motion artifact suppression processing method according to the first exemplary embodiment of the present disclosure.

Referring to FIG. 4, first, in step S401, the processing and computation module 304 places an otic bones exercise digital signal into a sample matrix.

Subsequently, in step S403, the processing and computation module 304 initializes a basis matrix and a coefficient matrix. For example, the processing and computation module 304 initializes the basis matrix and the coefficient matrix such that none of values of a plurality of elements in both matrices is a negative value. In other word, the values of the elements in the basis matrix and the coefficient matrix are all greater than or equal to 0.

In step S405, the processing and computation module 304 normalizes a column vector of the basis matrix until a sum of a plurality of elements corresponding to the column vector is 1.

In step S407, the processing and computation module 304 updates values of a plurality of elements of the basis matrix according to original values of the elements of the basis matrix. Subsequently, in step S409, the processing and computation module 304 updates values of a plurality of elements of the coefficient matrix according to original values of the elements of the coefficient matrix.

In step S411, the processing and computation module 304 determines whether the values of the elements in both the basis matrix and the coefficient matrix are fully updated.

If the values of the elements in both the basis matrix and the coefficient matrix are not yet fully updated, go back to step S407 and step S409, so that the processing and computation module 304 can re-execute the operation of updating the values of the elements of the basis matrix according to the original values of the elements of the basis matrix and updating the values of the elements of the coefficient matrix according to the original values of the elements of the coefficient matrix until the values of all the elements in the basis matrix and the coefficient matrix are fully updated.

If the values of the elements in both the basis matrix and the coefficient matrix are fully updated, in step S413, the processing and computation module 304 replaces the original values of the elements in both the basis matrix and the coefficient matrix respectively by the updated values of the elements.

In step S415, the processing and computation module 304 further normalizes the column vector of the basis matrix until the sum of the elements corresponding to the column vector is 1.

In step S417, the processing and computation module 304 further calculates a mean square error according to a product of the basis matrix and the coefficient matrix and the sample matrix.

Thereafter, in step S419, the processing and computation module 304 determines whether the mean square error is 0 or whether a value of the mean square error is no longer changing.

If the mean square error is not 0 or the value of the mean square error is constantly changing, go back to step S407 and step S409, so that the processing and computation module 304 can re-execute the operation of updating the values of the elements of the basis matrix according to the original values of the elements of the basis matrix and updating the values of the elements of the coefficient matrix according to the original values of the elements of the coefficient matrix until the values of all the elements in the basis matrix and the coefficient matrix are fully updated.

Otherwise, if the mean square error is 0 or the value of the mean square error is no longer changing, in step S421, the processing and computation module 304 obtains the motion artifact and the exercise heart rate signal according to the basis matrix, the coefficient matrix and the sample matrix.

In other words, the processing and computation module 304 will constantly execute an iterative operation until the motion artifact and the exercise heart rate signal are obtained. That is to say, "the value of the mean square error is constantly changing" herein refers to that the value of the mean square error obtained in the current iterative operation is different from the value of the mean square error obtained in the previous iterative operation; whereas "the value of the mean square error is no longer changing" herein refers to that the value of the mean square error obtained in the current iterative operation is identical to the value of the mean square error obtained in the previous iterative operation.

It should be noted that, the steps depicted in FIG. 4 may be implemented as a plurality of program codes or circuits, and the present disclosure is not limited thereto. For example, in another exemplary embodiment, the motion artifact suppression processing module 230 may be implemented by the hardware circuits to become a motion artifact suppression processing device, and the signal input module 302, the processing and computation module 304 and the signal output module 306 may be implemented by the hardware circuits to become a signal input circuit, a processing and computation circuit and a signal output circuit.

In addition, the decomposition for the motion artifact and the exercise heart rate signal in aforementioned motion artifact suppression processing method is performed by adopting characteristics of signal separation in single channel, a constraint condition with non-negative values for the elements, feature additivity and local characterization of non-negative values for the elements and an operational property consistent with neural network. Accordingly, the motion artifact may be effectively eliminated by using the motion artifact suppression processing method and device of the present disclosure in order to capture the stable exercise heart rate signal.

Figure 5:
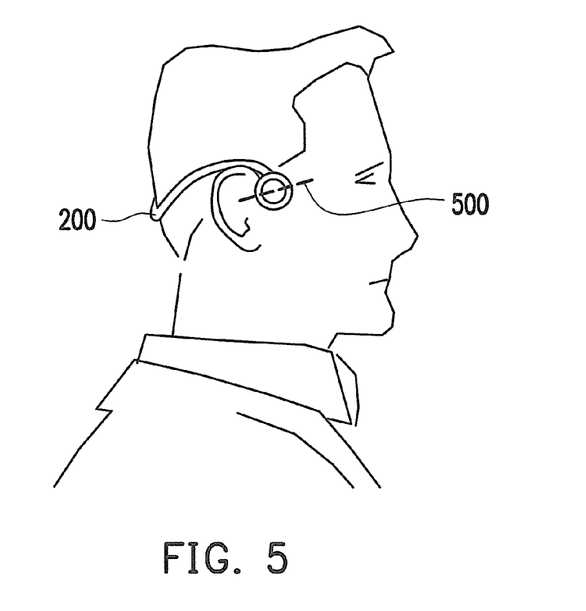
FIG. 5 is a schematic diagram illustrating detection of the physiological signal of the otic bones according to the first exemplary embodiment of the present disclosure.

FIG. 5 is a schematic diagram illustrating detection of the physiological signal of the otic bones according to the first exemplary embodiment of the present disclosure.

Referring to FIG. 5, an arterial system 500 at the otic bones of the human body operates in an otic bones region perpendicular to a carotid artery, and therefore a microvasculature will penetrate the otic bones. Further, during various exercises engaged in daily lives of people, positions around the otic bones or the ear are relatively more stable and have no intense actions, as compared to other body parts. That is to say, the otic bones are an ideal and stable part for exercise physiological sensing. In other words, a pulse rate can be obtained by detecting pulse beats at the otic bones. For example, in the exemplary embodiments of the present disclosure, in the operation of the front-end gain and filter module 210 for filtering and amplifying the physiological signal of the otic bones in order to generate the otic bones exercise analog signal, the front-end gain and filter module 210 captures a first heart sound signal from the received physiological signal of the otic bones to serve as the otic bones exercise analog signal. For instance, heart sounds are shock waves produced when blood pass through heart. Specifically, the heart sounds are shock waves produced when valve opens and closes, or vibrations caused by myocardial contract, closing of valve, and blood impacting ventricular wall, aorta wall and the like.

Figure 6:
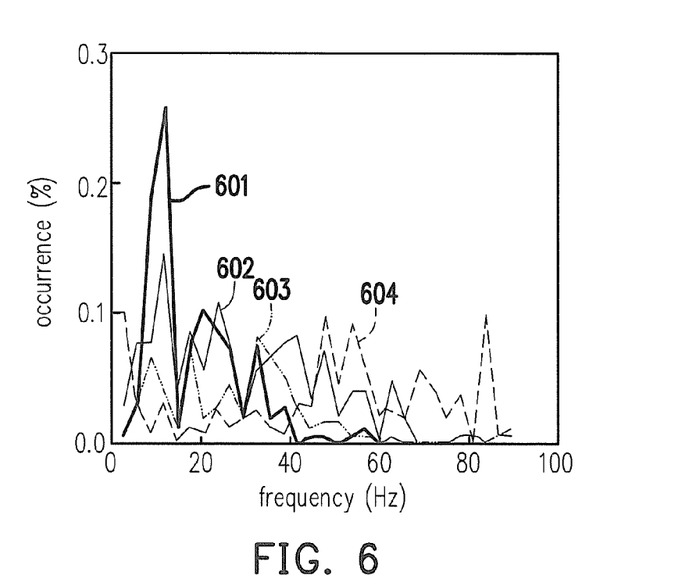
FIG. 6 is a schematic diagram illustrating a heart sound spectrum according to the first exemplary embodiment of the present disclosure.

FIG. 6 is a schematic diagram illustrating a heart sound spectrum according to the first exemplary embodiment of the present disclosure.

Referring to FIG. 6, two obvious heart sounds can be heard in a normal and healthy adult heart, and the two sounds sequentially occurs in each heart beat. A first of the two sounds is known as a first heart sound while a second of the two sounds is known as a second heart sound. The two heart sounds are produced by atrioventricular valve and semilunar valve, respectively. It is also possible that other sounds (e.g., murmur, a third sound being adventive sound, and a fourth heart sound with gallop rhythm) may occur in addition to said two normal sounds. The spectrum with four heart sounds as illustrated in FIG. 6 indicates frequencies for a first heart sound 601, a second heart sound 602, a third heart sound 603 and a fourth heart sound 604 to occur per one heart beat. In view of FIG. 6, it can be known that a spectral intensity of the first heart sound 601 is relatively greater, as compared to those of the second heart sound 602, the third heart sound 603 and the fourth heart sound 604. Therefore, for example, in the present exemplary embodiment, the front-end gain and filter module 210 captures the first heart sound signal to serve as the otic bones exercise analog signal. In addition, a cut-off frequency of the first heart sound 601 is approximately 16 Herz (Hz), and a signal frequency of the first heart sound 601 is below a sound frequency that the human ear can hear (20 Hz to 20000 Hz). Accordingly, the physiological signal of the user may be stably detected by the physiological sensor 204 (e.g., the bone conduction microphone).

Figure 7:
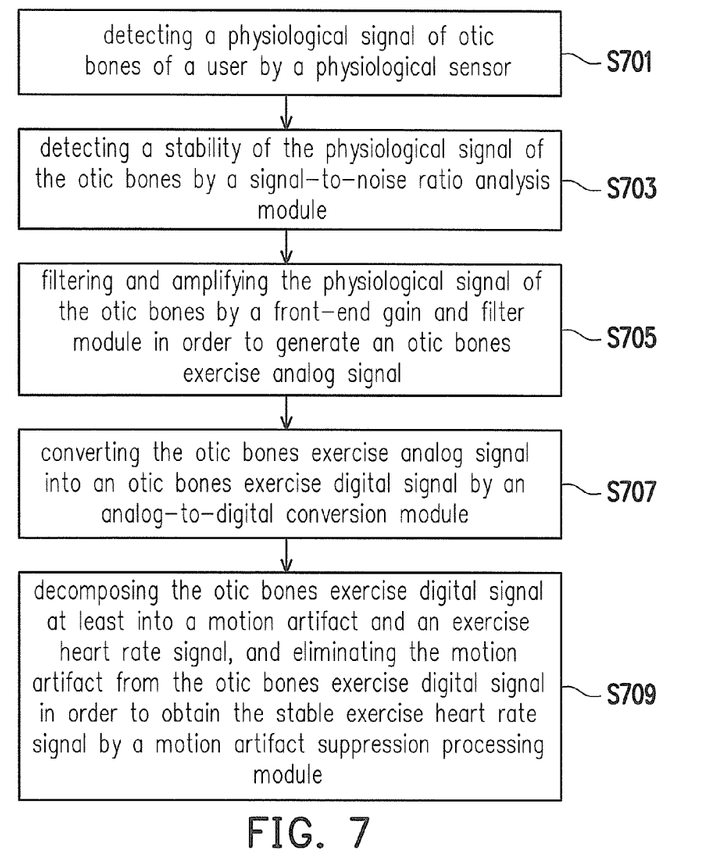
FIG. 7 is a flowchart illustrating an operation method of an exercise physiological sensing system according to the first exemplary embodiment of the present disclosure.

FIG. 7 is a flowchart illustrating an operation method of an exercise physiological sensing system according to the first exemplary embodiment of the present disclosure.

In step S701, the physiological sensor 204 (e.g., the bone conduction microphone) detects the physiological signal of the otic bones of the user. In step S703, the signal-to-noise ratio analysis module 102 detects a stability of the physiological signal of the otic bones. In step S705, the front-end gain and filter module 210 filters and amplifies the physiological signal of the otic bones in order to generate the otic bones exercise analog signal. In step S707, the analog-to-digital conversion module 220 converts the otic bones exercise analog signal into the otic bones exercise digital signal. Finally, in step S709, the motion artifact suppression processing module 230 decomposes the otic bones exercise digital signal at least into a motion artifact and an exercise heart rate signal, and eliminates the motion artifact from the otic bones exercise digital signal in order to obtain the stable exercise heart rate signal.

Steps depicted in FIG. 7 are described in detail as above, thus it is omitted hereinafter. It should be noted that, each of the steps depicted in FIG. 7 may be implemented as a plurality of circuits, or step S709 in FIG. 7 may be implemented as a plurality of program codes, and the present disclosure is not limited thereto. Moreover, the method disclosed in FIG. 7 may be used together with the foregoing embodiments, or may be used alone, and the present disclosure is not limited thereto.

[Second Exemplary Embodiment]

An exercise physiological sensing system of the second exemplary embodiment and an operation method thereof are essentially identical to the physiological sensing system of the first exemplary embodiment and the operation method thereof, and a difference between the two embodiments is that a physiological sensor used in the second exemplary embodiment is a micro electrical-mechanical system (MEMS) microphones. The difference between the second exemplary embodiment and the first exemplary embodiment is described below by reference with system and device structures depicted in FIG. 1, FIG. 2A to FIG. 2B, FIG. 3 and FIG. 8.

Referring back to FIG. 1, in the present exemplary embodiment, the physiological sensor 204 is the MEMS microphone, and the physiological sensor 204 is capable of detecting the physiological signal of the otic bones of the user. The signal-to-noise ratio analysis module 102 detects a stability of the physiological signal of the otic bones received by the physiological sensor 204. Further, the computation module 106 generates the stable exercise heart rate signal according to the physiological signal of the otic bones received by the physiological sensor 204. It should be noted that, in this exemplary embodiment, because the physiological sensor is the MEMS microphone, the physiological sensor of the otic bones being detected has lower stability and high noise. Accordingly, the signal-to-noise ratio analysis module 102 may determine that the quality of the physiological signal of the otic bones is poor.

Figure 8:
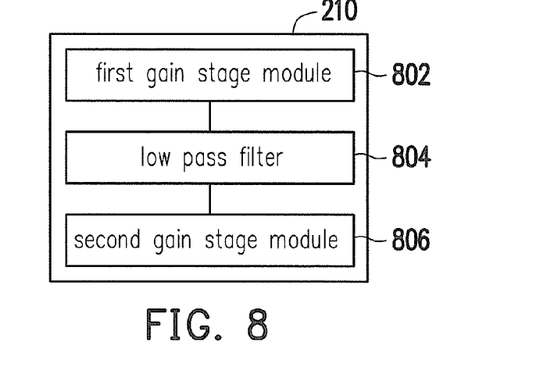
FIG. 8 is a block diagram illustrating a front-end gain and filter module according to a second exemplary embodiment of the present disclosure.

FIG. 8 is a block diagram illustrating a front-end gain and filter module according to a second exemplary embodiment of the present disclosure.

Referring to FIG. 8, the front-end gain and filter module 210 further includes a first gain stage module 802, a low pass filter 804 and a second gain stage module 806. Based on the above, since the physiological sensor of the otic bones detected by the MEMS microphone has lower stability and high noise, in the present exemplary embodiment, the first gain stage module 802 in the front-end gain and filter module 210 may first amplify the physiological signal of the otic bones. Subsequently, the otic bones exercise analog signal may then be captured by the low pass filter 804 from the amplified physiological signal of the otic bones. Herein, the otic bones exercise analog signal captured by the low pass filter 804 is the first heart sound signal which cutoff frequency is 16 Hz. Thereafter, the second gain stage module 806 may amplify the otic bones exercise analog signal in order to improve the stability of the otic bones exercise analog signal.

Thereafter, as identical to the first exemplary embodiment, the analog-to-digital conversion module 220 converts the processed otic bones exercise analog signal into an otic bones exercise digital signal, and transmits this otic bones exercise digital signal to the motion artifact suppression processing module 230. The motion artifact suppression processing module 230 decomposes the otic bones exercise digital signal at least into a motion artifact and an exercise heart rate signal, and eliminates the motion artifact from the otic bones exercise digital signal in order to obtain the stable exercise heart rate signal. Herein, detailed steps executed by the motion artifact suppression processing module 230 for obtaining the stable exercise heart rate signal are identical to those in the motion artifact suppression process method of the first exemplary embodiment, which are not repeated hereinafter.

It should be noted that, in the present disclosure, the front-end gain and filter module 210 as well as the first gain stage module 802 and the second gain stage module 806 thereof may be implemented by the hardware circuits to become the front-end gain and filter circuit, the first gain stage circuit and the second gain stage circuit.

Figure 9:
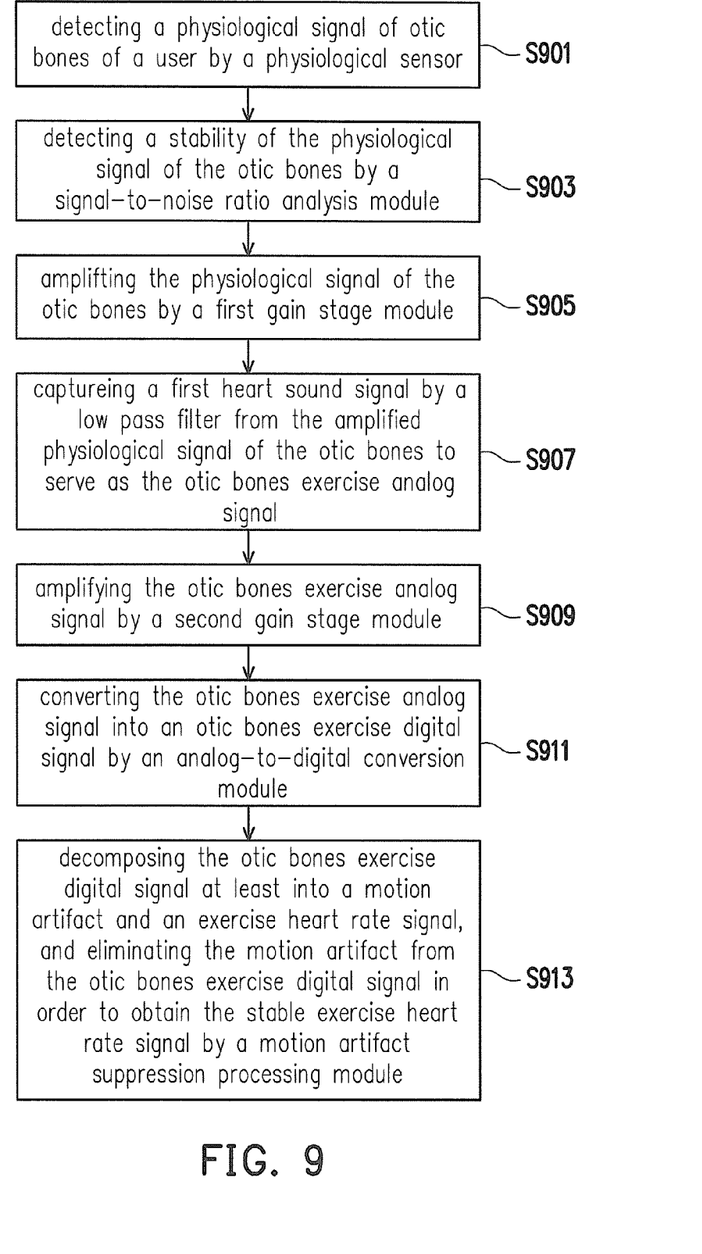
FIG. 9 is a flowchart illustrating an operation method of the exercise physiological sensing system according to the second exemplary embodiment of the present disclosure.

FIG. 9 is a flowchart illustrating an operation method of the exercise physiological sensing system according to the second exemplary embodiment of the present disclosure.

First, in step S901, the physiological sensor 204 (e.g., the MEMS microphone) detects the physiological signal of the otic bones of the user. Subsequently, in step S903, the signal-to-noise ratio analysis module 102 detects a stability of the physiological signal of the otic bones. Particularly, in the present exemplary embodiment, in step S905, the first gain stage module 802 in the front-end gain and filter module 210 amplifies the physiological signal of the otic bones. In step S907, the low pass filter 804 captures the first heart sound signal from the amplified physiological signal of the otic bones to serve as the otic bones exercise analog signal. Further, in step S909, the second gain stage module 806 amplifies the otic bones exercise analog signal. Thereafter, in step S911, the analog-to-digital conversion module 220 converts the otic bones exercise analog signal into the otic bones exercise digital signal. Finally, in step S913, the motion artifact suppression processing module 230 decomposes the otic bones exercise digital signal at least into a motion artifact and an exercise heart rate signal, and eliminates the motion artifact from the otic bones exercise digital signal in order to obtain the stable exercise heart rate signal.

Steps depicted in FIG. 9 are described in detail as above, thus it is omitted hereinafter. It should be noted that, each of the steps depicted in FIG. 9 may be implemented as a plurality of circuits, or step S913 in FIG. 9 may be implemented as a plurality of program codes, and the present disclosure is not limited thereto. Moreover, the method disclosed in FIG. 9 may be used together with the foregoing embodiments, or may be used alone, and the present disclosure is not limited thereto.

In summary, the exercise physiological sensing system, the motion artifact suppression processing method and device according to the present disclosure are capable of providing lightweight and comfortability for the user during exercise as well as effectively improving the stability of the exercise physiological data detected in the high-intensity exercise training by detecting the physiological signal of the otic bones of the user. In addition, the exercise physiological sensing system, the motion artifact suppression processing method and device according to the present disclosure are also capable of providing the functions to play music or radio programs for the user while constantly monitoring the physiological status of the user. Particularly, since the exercise physiological sensing system and the motion artifact suppression processing device are disposed at the otic bones of the user, the user is also able to be aware of surrounding sounds accordingly, so that the safety during exercise can be improved.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. An exercise physiological sensing system for obtaining a stable exercise heart rate signal of a user during exercise, the exercise physiological sensing system comprising:
   a bone conduction object having a physiological sensor, wherein the physiological sensor detects a physiological signal of otic bones of the user;
   a signal-to-noise ratio analysis module coupled to the physiological sensor, wherein the signal-to-noise ratio analysis module detects a stability of the physiological signal of the otic bones; and
   a computation module coupled to the signal-to-noise ratio analysis module, wherein the computation module generates the stable exercise heart rate signal according to the physiological signal of the otic bones,
   wherein the computation module further comprises:
      a front-end gain and filter module filtering and amplifying the physiological signal of the otic bones to generate an otic bones exercise analog signal;
      an analog-to-digital conversion module converting the otic bones exercise analog signal into an otic bones exercise digital signal; and
      a motion artifact suppression processing module decomposing the otic bones exercise digital signal at least into a motion artifact and an exercise heart rate signal, and eliminating the motion artifact from the otic bones exercise digital signal to obtain the stable exercise heart rate signal,
   wherein in the operation of decomposing the otic bones exercise digital signal at least into the motion artifact and the exercise heart rate signal, the motion artifact suppression processing module places the otic bones exercise digital signal into a sample matrix, and execute an iterative operation until the motion artifact and the exercise heart rate signal are obtained,
   wherein the motion artifact suppression processing module further initializes a basis matrix and a coefficient matrix, wherein values of a plurality of elements in both the basis matrix and the coefficient matrix are not negative values,
   wherein the motion artifact suppression processing module further normalizes a column vector of the basis matrix until a sum of a plurality of elements corresponding to the column vector is 1,
   wherein the motion artifact suppression processing module further updates the values of the elements of the basis matrix according to original values of the elements of the basis matrix and updates the values of the elements of the coefficient matrix according to original values of the elements of the coefficient matrix,
   wherein if the values of the elements in both the basis matrix and the coefficient matrix are fully updated, the motion artifact suppression processing module further replaces the original values of the elements in both the basis matrix and the coefficient matrix respectively by the updated values of the elements,
   wherein if the values of the elements in both the basis matrix and the coefficient matrix are not yet fully updated, the motion artifact suppression processing module re-executes the operation of updating the values of the elements of the basis matrix according to the original values of the elements of the basis matrix and updating the values of the elements of the coefficient matrix according to the original values of the elements of the coefficient matrix,
   wherein the motion artifact suppression processing module further normalizes the column vector of the basis matrix until the sum of the elements corresponding to the column vector is 1,
   wherein the motion artifact suppression processing module further calculates a mean square error according to a product of the basis matrix and the coefficient matrix and the sample matrix,
   wherein if the mean square error is 0 or a value of the mean square error is no longer changing, the motion artifact suppression processing module obtains the motion artifact and the exercise heart rate signal according to the basis matrix, the coefficient matrix and the sample matrix, wherein if the mean square error is not 0 or the value of the mean square error is constantly changing, the motion artifact suppression processing module re-executes the operation of updating the values of the elements of the basis matrix according to the original values of the elements of the basis matrix and updating the values of the elements of the coefficient matrix according to the original values of the elements of the coefficient matrix.

2. The exercise physiological sensing system as claimed in claim 1, wherein the front-end gain and filter module further captures a first heart sound signal from the received physiological signal of the otic bones to serve as the otic bones exercise analog signal.

3. The exercise physiological sensing system as claimed in claim 2, wherein the front-end gain and filter module further comprises a first gain stage module, a second gain stage module and a low pass filter, wherein the first gain stage module amplifies the physiological signal of the otic bones, wherein the low pass filter captures another first heart sound signal from the amplified physiological signal of the otic bones to serve as the otic bones exercise analog signal, wherein the second gain stage module amplifies the otic bones exercise analog signal.

4. The exercise physiological sensing system as claimed in claim 2, wherein a cut-off frequency of the first heart sound signal is 16 Hz.

5. The exercise physiological sensing system as claimed in claim 1, wherein the physiological sensor is a bone conduction microphone.

6. The exercise physiological sensing system as claimed in claim 1, wherein the physiological sensor is a micro electrical-mechanical system microphone.

* * * * *